(12) United States Patent
Covington et al.

(10) Patent No.: US 6,569,089 B1
(45) Date of Patent: May 27, 2003

(54) LIGHTED INTUBATING LARYNGOSCOPE

(76) Inventors: Roy Covington, P.O. Box 7313, Ruidoso, NM (US) 88355; Robert Gorman, 8317 San Miguel Ct., NE., Albuquerque, NM (US) 87109

( * ) Notice: Subject to any disclaimer, the term of this patent is extended or adjusted under 35 U.S.C. 154(b) by 0 days.

(21) Appl. No.: 09/729,135

(22) Filed: Dec. 1, 2000

Related U.S. Application Data

(60) Provisional application No. 60/168,992, filed on Dec. 3, 1999.

(51) Int. Cl.$^7$ ............................................... A61B 1/267
(52) U.S. Cl. ...................................... 600/199; 604/264
(58) Field of Search ................. 604/264, 282; 600/185, 199, 188, 191

(56) References Cited

U.S. PATENT DOCUMENTS

| | | | |
|---|---|---|---|
| 4,126,127 A | | 11/1978 | May |
| 4,681,094 A | * | 7/1987 | Rolnick ........................ 128/10 |
| 5,183,031 A | | 2/1993 | Rossoff |
| 5,337,735 A | * | 8/1994 | Salerno ........................ 128/11 |
| 5,355,870 A | * | 10/1994 | Lacy ............................. 128/11 |
| 5,381,787 A | * | 1/1995 | Bullard ........................ 128/11 |
| 5,394,865 A | * | 3/1995 | Salerno ........................ 128/11 |
| 5,413,092 A | * | 5/1995 | Williams, III et al. .......... 128/6 |
| 5,580,147 A | * | 12/1996 | Salerno ........................ 600/199 |
| 5,665,052 A | * | 9/1997 | Bullard ........................ 600/194 |
| 5,772,581 A | * | 6/1998 | Gaines ........................ 600/197 |
| 5,845,634 A | * | 12/1998 | Parker ........................ 600/153 |
| 5,897,489 A | | 4/1999 | Urbanowicz et al. |
| 6,146,402 A | * | 11/2000 | Munoz ........................ 606/194 |
| 6,176,824 B1 | * | 1/2001 | Davis ........................ 600/178 |

* cited by examiner

*Primary Examiner*—Edward K. Look
*Assistant Examiner*—Dwayne White
(74) *Attorney, Agent, or Firm*—Katy C. Fain; Deborah A. Peacock; Jeffrey D. Myers (57) ABSTRACT

The present invention is an intubating laryngoscope with light provided to the suction tip or blade simultaneously during intubation. Preferably, the laryngoscope is made of a transparent, engineering plastic material to provide a light path for light from a light source (e.g. flashlight). In an alternative embodiment, light is provided to the suction tip by fiber optics.

29 Claims, 7 Drawing Sheets

LIGHTED INTUBATING LARYNGOSCOPE

CROSS-REFERENCE TO RELATED APPLICATIONS

This application claims the benefit of the filing of U.S. Provisional Patent Application Ser. No. 60/168,992, entitled "Intubating Laryngoscope" filed on Dec. 3, 1999, and the specification thereof is incorporated herein by reference.

BACKGROUND OF THE INVENTION

1. Field of the Invention (Technical Field)

The present invention relates to a self-contained, lighted laryngoscope for clearing and visualizing the intubation pathway.

2. Background Art

Health care providers perform direct laryngoscopy to either clear a patient's airway of debris, or more commonly place a tube into a patient's trachea to assist or replace a patient's ability to oxygenate his/her system. The laryngoscope utilizes either a straight or curved blade that allows visualization of the vocal cords, which are the landmarks for locating the opening of the trachea. This lighted blade is used to keep the tongue from obstructing the provider's view of the vocal cords. The tip of the blade lifts the epiglottis, thereby providing a direct view into the patient's trachea, and reducing the risk of intubating the esophagus instead. Intubation and blowing air into the stomach is not useful, causes stomach distention and vomiting, and furthermore, unless recognized quickly deprives the patient of much needed oxygen and causes an associated increase in morbidity.

Proper placement of the laryngoscope is often hindered by the presence of blood, saliva, vomit, secretions, or broken teeth in people who have sustained injuries or sickness.

Intubation itself requires two hands. One hand operates the lighted laryngoscope in order to visualize the vocal cords and the opening to the trachea, and the other hand places the tube. In a trauma situation, the patient's mouth may be filled with the aforementioned debris. Often, another person is required to suction out the debris in the oral cavity. There are numerous ways to handle this urgent situation, all having their own disadvantages. Following are some of the most frequently seen scenarios:

(a) The person must put the tube down, grasp for the suction catheter, clear the airway, place the suction device down into the airway, clearing it, and then regrasp and place the tube. During the process of regrasping the tube, the view of the airway aperture is occasionally lost. The procedure must then be repeated from the beginning, losing valuable time as well as depriving the patient of oxygen. The patient must then be ventilated for 15 to 30 seconds by basic means whereby oxygen is forced through the patient's nose and mouth into his lungs. Some air also goes into the stomach. Eventually, the stomach becomes so distended by air that it empties through the mouth. This in turn requires constant and aggressive suctioning to allow a clear view down the airway for another attempt at intubation to be made. Each additional attempt causes the patient to further asphyxiate due to hypoxia, or lack of oxygen. Other disadvantages of additional attempts are cosmetic injuries to teeth, gums, and lips. Injuries to these areas increase as the number of attempts increase.

(b) A second health care provider can provide suctioning while the person visualizing the airway maintains his view of the airway aperture. In today's health care market, personnel cuts often result in shortages of personnel. There may not be a team member available to do this.

(c) Frequently, after repeating this procedure unsuccessfully, health care providers are forced out of necessity to perform an emergency cricothyrotomy. Although a relatively easy procedure, if not performed by skilled personnel with intricate knowledge of the human airway, it can be fatal within seconds. There is also a chance of post-procedure infection.

Several prior art devices have attempted to address some of these shortcomings:

U.S. Pat. No. 4,126,127, to May, entitled "Suctioning/Oxygenating Laryngoscope Blade," discloses a laryngoscope having a suction tube down the side, with a battery-powered light and sighting channel underneath, but not at the suction tip.

U.S. Pat. No. 5,183,031, to Rossoff, entitled "Fiberoptic Intubating Laryngoscope," discloses a fiberoptic flexible stylet and suction channel manipulable by a cable attached to a pistol grip. A syringe port is used for the suction or instillation of fluid. The fiber optics stylet is initially placed in the syringe port to view the patient's larynx for positioning of the laryngoscope. Once correct positioning is established, the fiber optics stylet is withdrawn so that suctioning can occur.

U.S. Pat. No. 5,897,489, to Urbanowicz et al., entitled "Snap-On Suction Tube For Laryngoscope," discloses a suction device with a flexible tip that clips onto a laryngoscope. A battery operates a light through the laryngoscope.

SUMMARY OF THE INVENTION (DISCLOSURE OF THE INVENTION)

The present invention is a lighted intubating laryngoscope comprising a hand-held end, a suction tip and an suction channel within a casing; and a light source outside the suction channel, the light source activated and operable by a single operator at the hand-held end for providing light to the suction tip while the laryngoscope is intubating a patient. The preferred light source is a flashlight attached to the hand-held end by an adhesive, clamp, shrink wrap, or other attachment means. Preferably, the flashlight is activated by a push button. In the preferred embodiment, the suction channel casing is made of a light-carrying material, such as a transparent material, preferably an engineering plastic material, and most preferably a polycarbonate resin material.

In an alternative embodiment, the light source comprises fiber optics.

In one embodiment, the suction tip comprises a detachable suction tip. This tip may be attached to the suction channel by an adhesive. The suction tip may be made of a light-carrying material and provides diffused light or other type of illumination depending upon the configuration at the suction tip.

The present invention is further directed to a method of providing light to an intubating laryngoscope procedure comprising: providing an intubating laryngoscope comprising a hand-held end, a suction tip and an suction channel within a casing; providing a light source (e.g. flashlight or fiber optics) outside the suction channel, the light source activatable and operable by a single operator at the hand-held end for providing light to the suction tip; and intubating a patient while simultaneously providing the light source to the suction tip.

In one embodiment, there is a detachable tip. The operator selects a detachable tip suitable for the age or size of the patient.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

A preferred embodiment of the present invention is a laryngoscope comprising a light source (e.g., flashlight or fiber optic) and a single cylinder laryngoscope containing suction openings. The apparatus is preferably rigid, and is preferably made of a transparent, engineering plastic (e.g. polycarbonate resin), although other materials such as stainless steel, metals, ceramics, composites or other plastics, may be used. With a transparent material, the intubation tube itself is used as the light passage and delivery medium. The apparatus is easily operable by one user.

The device affords a lighted view of a patient's airway combined with a suction conduit, and eliminates the need for the currently used Yankauer suction tip and the third hand. The suction ports are preferably large enough to remove debris or articles as large as a kernel of corn without clogging. While the airway is being cleared, lighted visualization of the airway is simultaneously occurring.

The preferred embodiment of the invention is shown in FIGS. 1–4. As shown therein, the apparatus of the present invention comprises a hand-held end 10, a suction tip 12, a light source 14, such as a flashlight, an suction channel 16, and a casing 18 surrounding the suction channel 16. Vacuum suction is provided from tip 12 to hand-held end 10 of debris or fluids from a patient's airway while light from light source 14 is simultaneously provided to suction tip 12. Suction port 28 allows the operator to regulate or modulate the amount of suction. A vacuum tube attachment barb 32 may also be provided to accommodate a vacuum pump or suction device.

The apparatus of the present invention may be of any standard or custom shape and size. Likewise, suction tip 12 or blade may be of various shapes and sizes depending on the application. Suction tip 12 or blade may have one or a plurality of suction ports.

In the preferred embodiment of the present invention, casing 18 is made of a light-carrying, transparent material, such as an engineering plastic (e.g. polycarbonate resin, often known as Lexan). Engineering plastic materials allow for an inexpensive laryngoscope apparatus to be manufactured, allowing the apparatus to be disposed of after use. This light-carrying material allows the light to travel from light source 14 at light source application point 20 where the light is carried through the light-carrying casing 18 (not into suction channel 16) all the way to suction tip 12 because of the transparency. This light-carrying casing provides a light path so that the light goes along casing 18 (which surrounds suction channel 16) to suction tip 12. When the light exits suction tip 12, it is preferably diffuse for better viewing for placement or operation of suction 12 and the laryngoscope. The light application point 20 may be a port or opening through the casing 18, but need not be, as the light to be transmitted in the preferred embodiment passes freely through the transparent material of the casing 18. It is evident therefore, that a very distinct advantage of a preferred embodiment of the apparatus 10 of the invention is that the material of the casing 18 itself functions as the medium by which light travels to the suction tip 12. Accordingly, the need is eliminated for light to actually pass down the channel 16 for purposes of illuminating conditions in the vicinity of the suction tip 12. Rather, the casing itself functions as a light conduit directing illumination to where it is needed most, even when matter is passing through the channel 16. As can be appreciated by those skilled in the art, the apparatus 10 thus does not require a separate, bulky channel to provide light to suction tip 12.

Light source 14 is preferably provided by a flashlight, available in the art, that has a push-button on/off switch 22. This switch 22 is activated by the operator at hand-held end 10 while simultaneously operating the laryngoscope. Although a push-button switch is shown in the drawings, other activation means may be utilized (e.g. slide, twist, etc.). A light bulb 24 emits light from flashlight 14 into light application point 20. Light application point 20 is designed at a critical angle 34 to allow light to be emitted from light-carrying material 18. This angle depends on the specific light-carrying material 18 utilized, light source 14, and positioning of light source 14.

Figure 1:
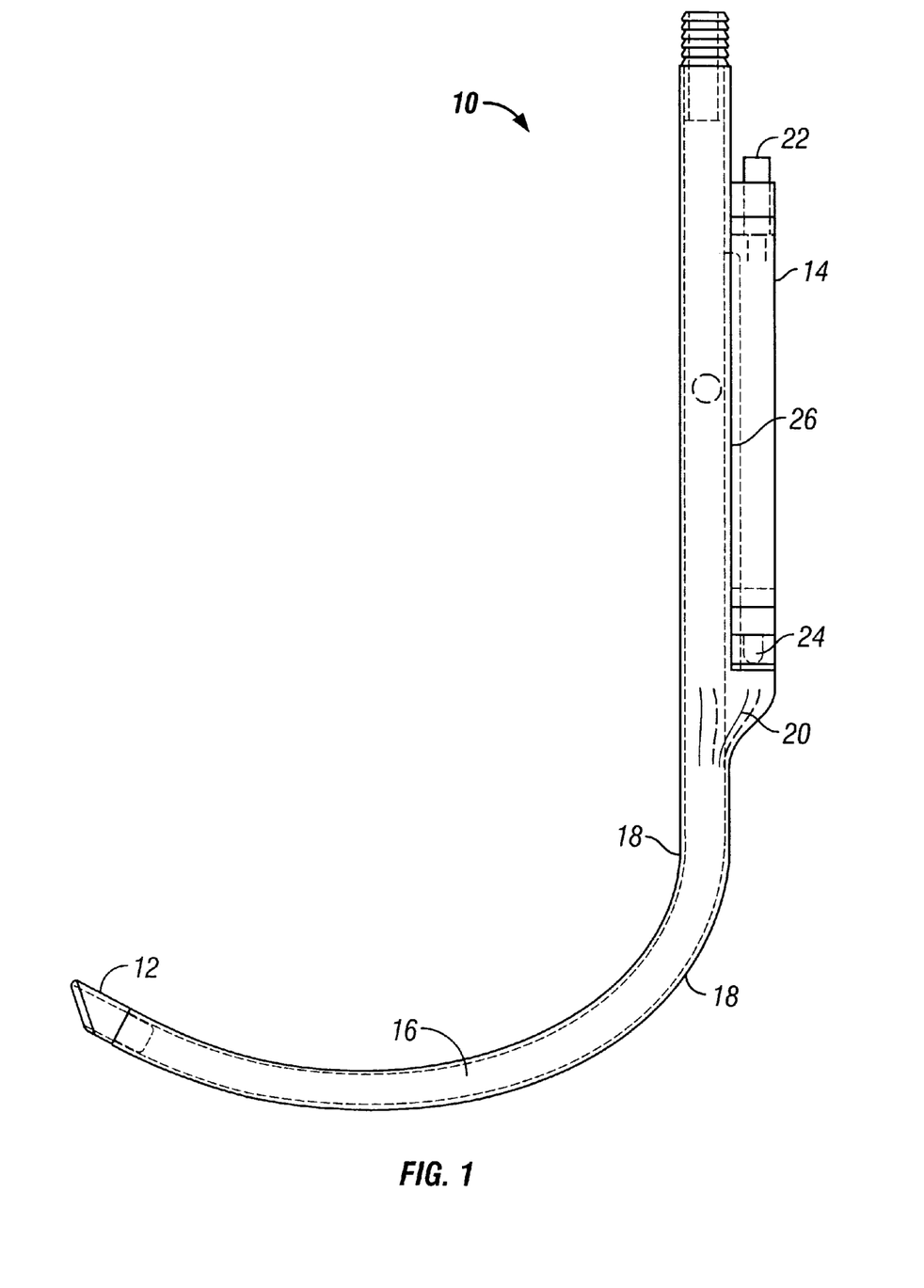
FIG. 1 is a side view of the preferred laryngoscope of the present invention.
Figure 2:
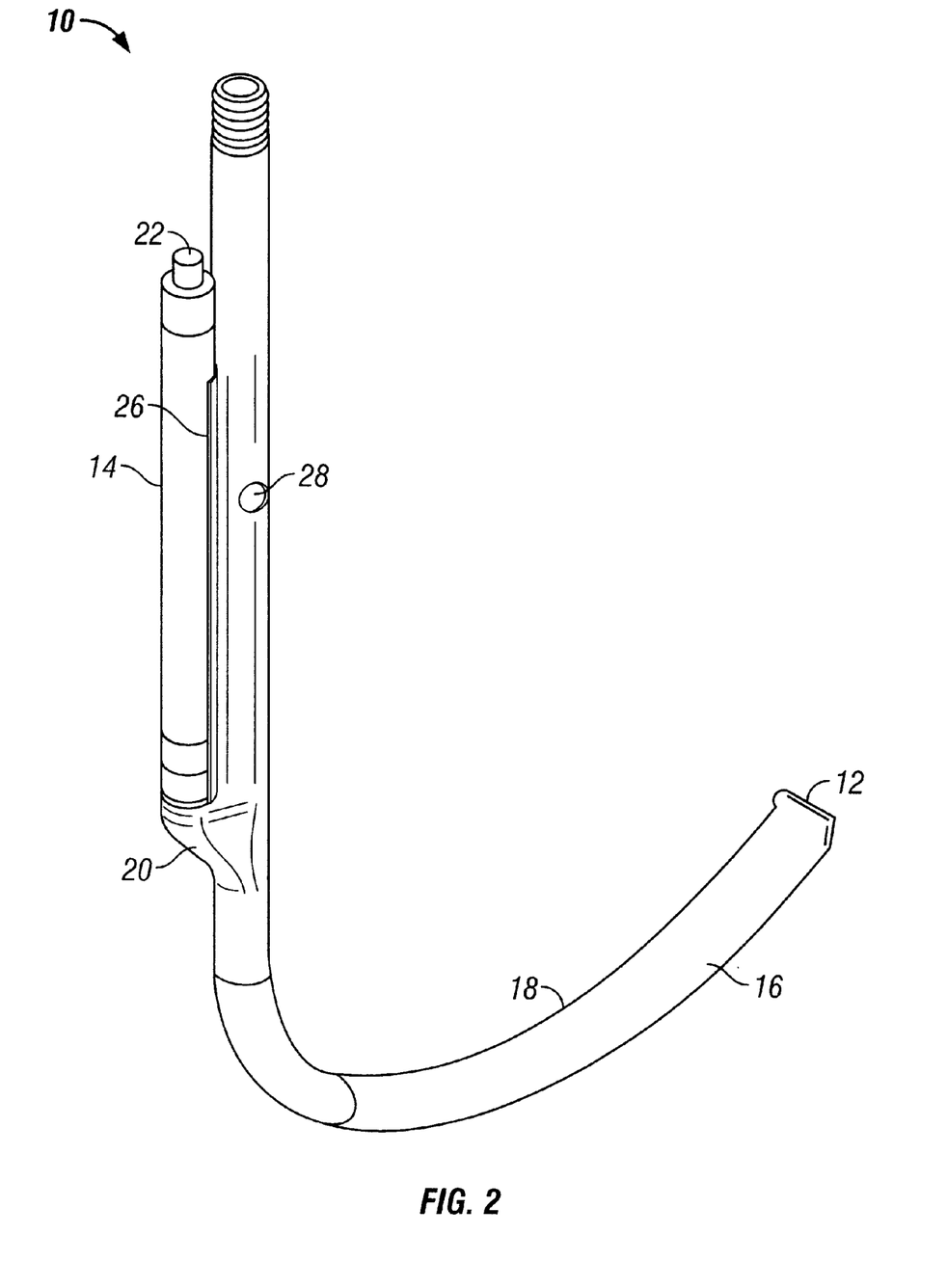
FIG. 2 is a perspective rear view of the preferred embodiment of FIG. 1.
Figure 3:
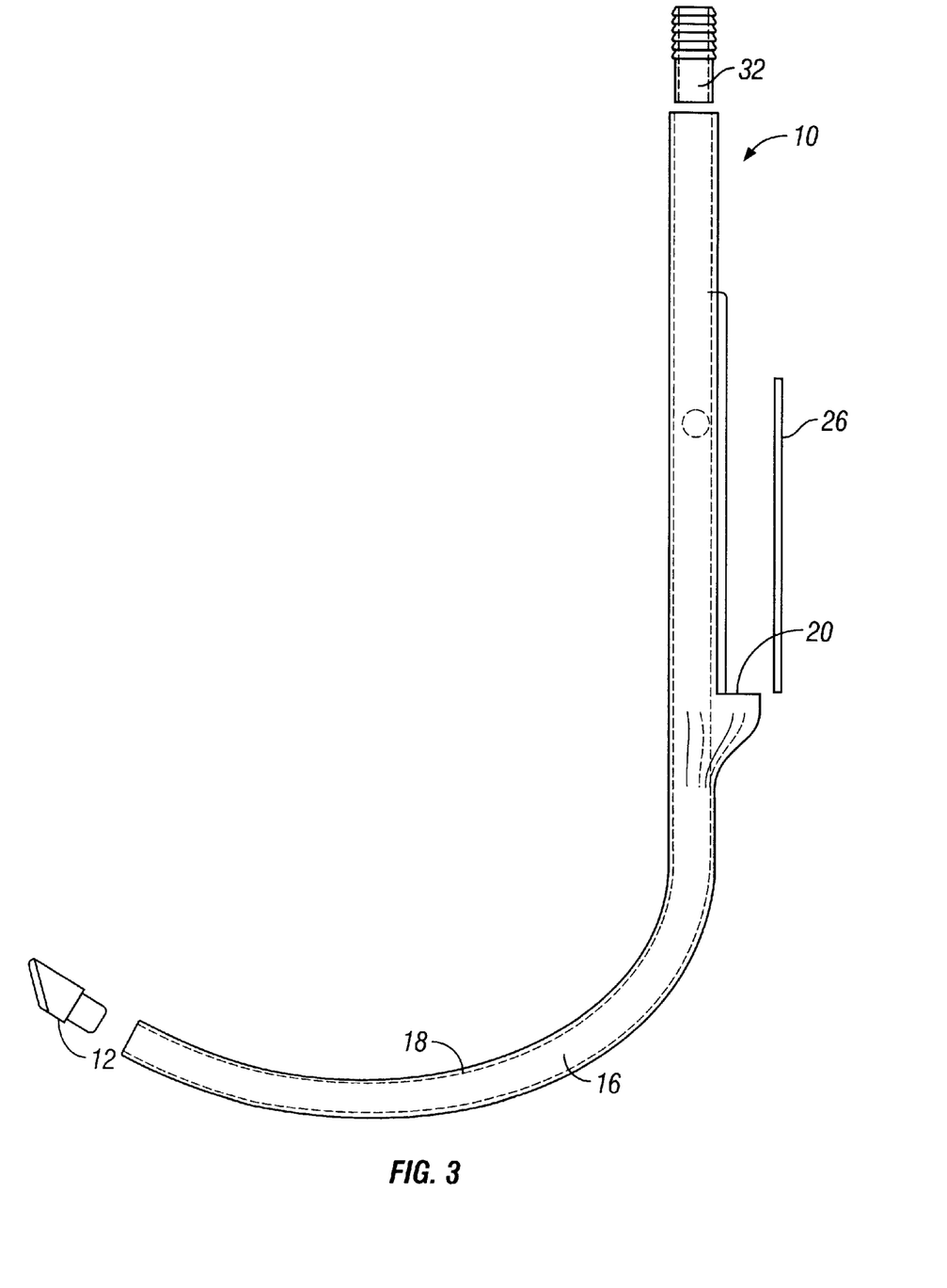
FIG. 3 is an expanded side view of the embodiment of FIG. 1.
Figure 4:
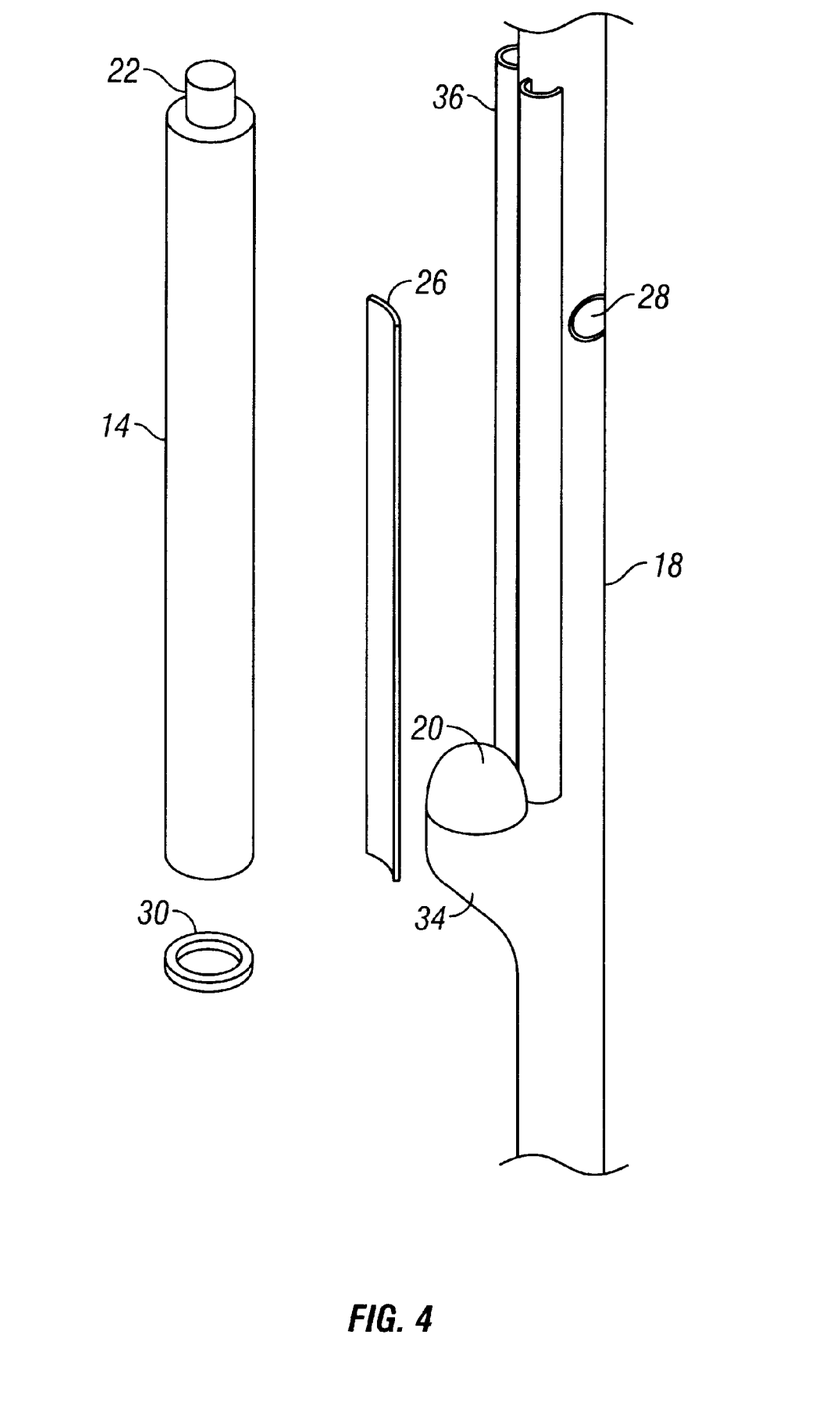
FIG. 4 is an expanded perspective view of the flashlight area of the embodiment of FIG. 1.

Flashlight 14 is shown attached to casing 18 at hand-held end 10 by an adhesive 26 (e.g. double-sided adhesive), although other attachment means may be provided, such as a clip, band, strap, shrink-wrap, and the like. Preferably, flashlight 14 is off-the-shelf so it can be easily replaced or moved from laryngoscope to laryngoscope if the laryngoscope is disposable. FIGS. 3 and 4 are exploded views showing flashlight 14 attached to casing 18 via adhesive 26. Light seal pad 30 provides a seal between flashlight 14 and light application point 20. Casing 18 may be specifically configured 36 to accommodate a particular flashlight shape.

Figure 5:
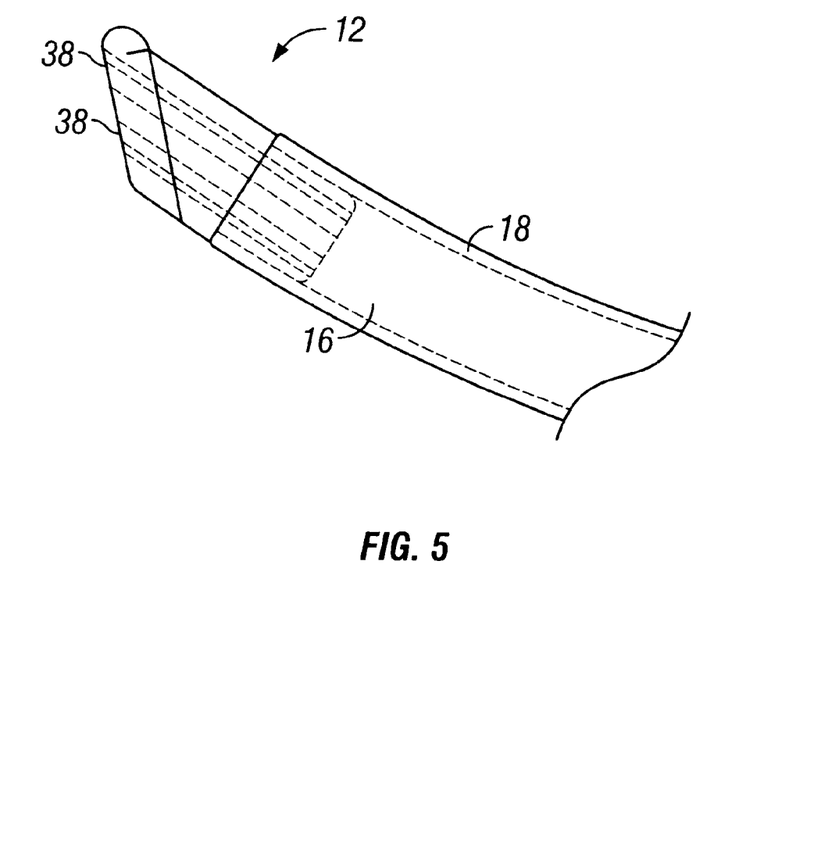
FIG. 5 is a detail side view of a preferred interchangeable suction tip.
Figure 6:
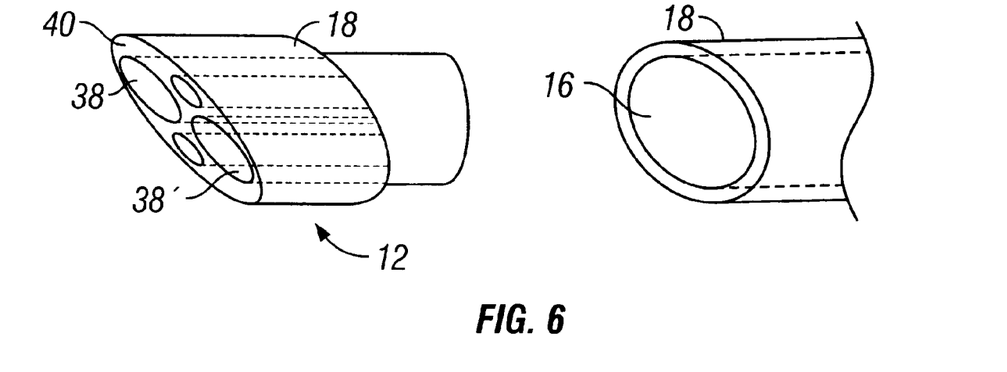
FIG. 6 is a perspective view of the interchangeable suction tip detached from the casing.

FIGS. 5 and 6 show details of the preferred suction tip 12 of the present invention. Suction tip 12 may be integral with casing 18 or separately interchangeable, i.e. attachable to and detachable from casing 18. If suction tip 12 is detachable, it is preferably attached to casing 18 via an adhesive or glue so that it does not dislodge during use. The advantage of a separable attachable suction tip 12 is that it can be chosen based on the patient's age, size, or situation. For instance, a small suction tip may be chosen for a child and a large suction tip chosen for an adult. Likewise, suction tips with large holes may be chosen for a particular application. The emergency medical technician or operator may have a series of different suction tips which can be readily accessed for use. FIG. 5 shows suction tip 12 with various suction ports 38, 38'. Suction tip 12 is attached to casing 18.

FIG. 6 shows casing 18 and suction tip 12 separated whereby suction tip 12 fits into casing 18. As can be appreciated by those skilled in the art, the apparatus may also be configured so that the suction tip fits over the casing.

Suction tip 12 is preferably also made of a light-carrying, transparent material (e.g. polycarbonate resin) so that the light continues to be transported to the end 40 of the suction tip 12 for viewing. End 40 of suction tip 12 may be angled or configured to provide different light properties, and act as a "lens." Preferably the light is scattered or diffused at end 40, although for some applications, suction tip 12 or casing 18 may be modified to provide different light characteristics or illumination, such as a pin-point light, a beam with a particular radius, and the like.

Figure 7:
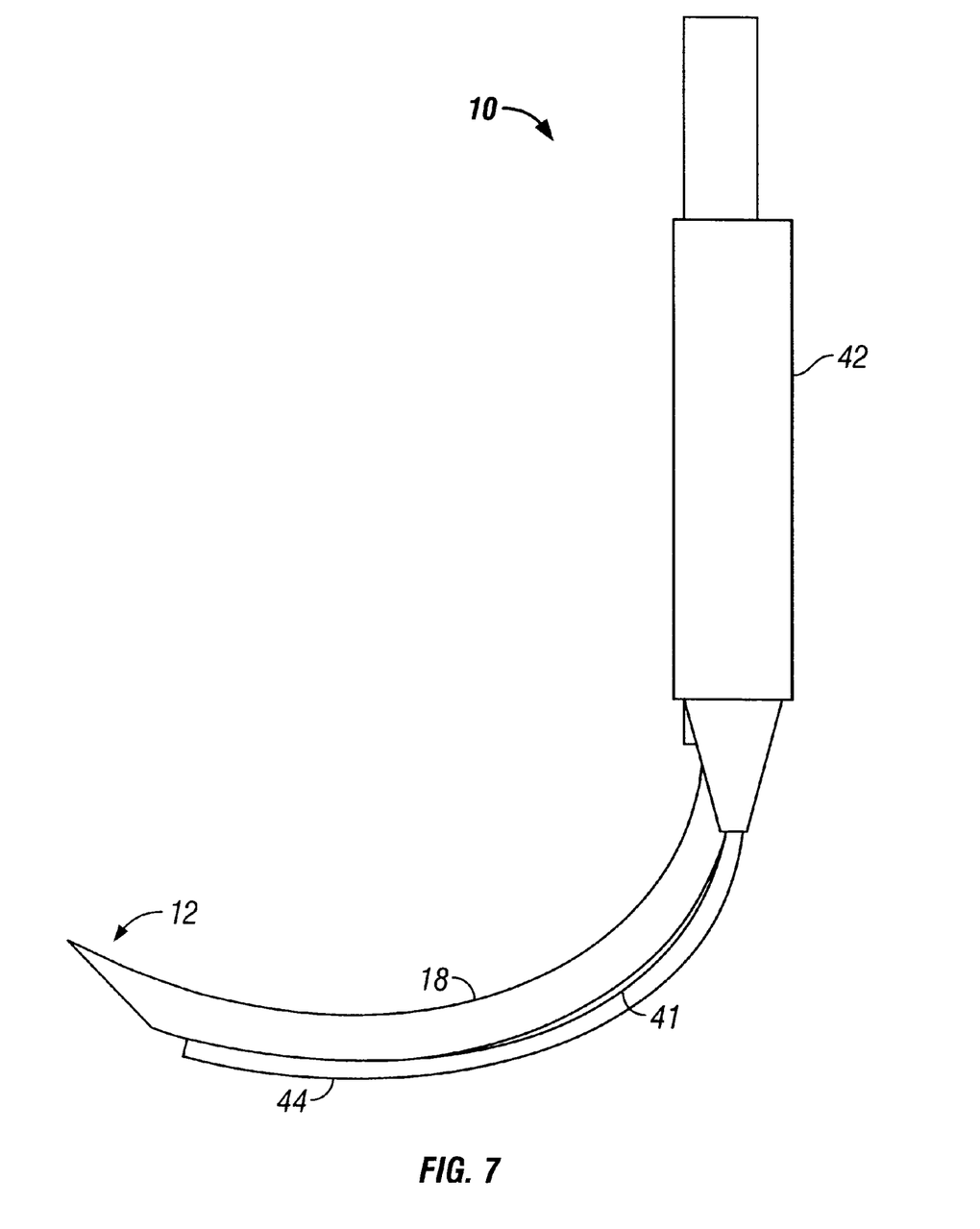
FIG. 7 is a side view of an alternative embodiment of the present invention showing use of fiber optics.
Figure 8:
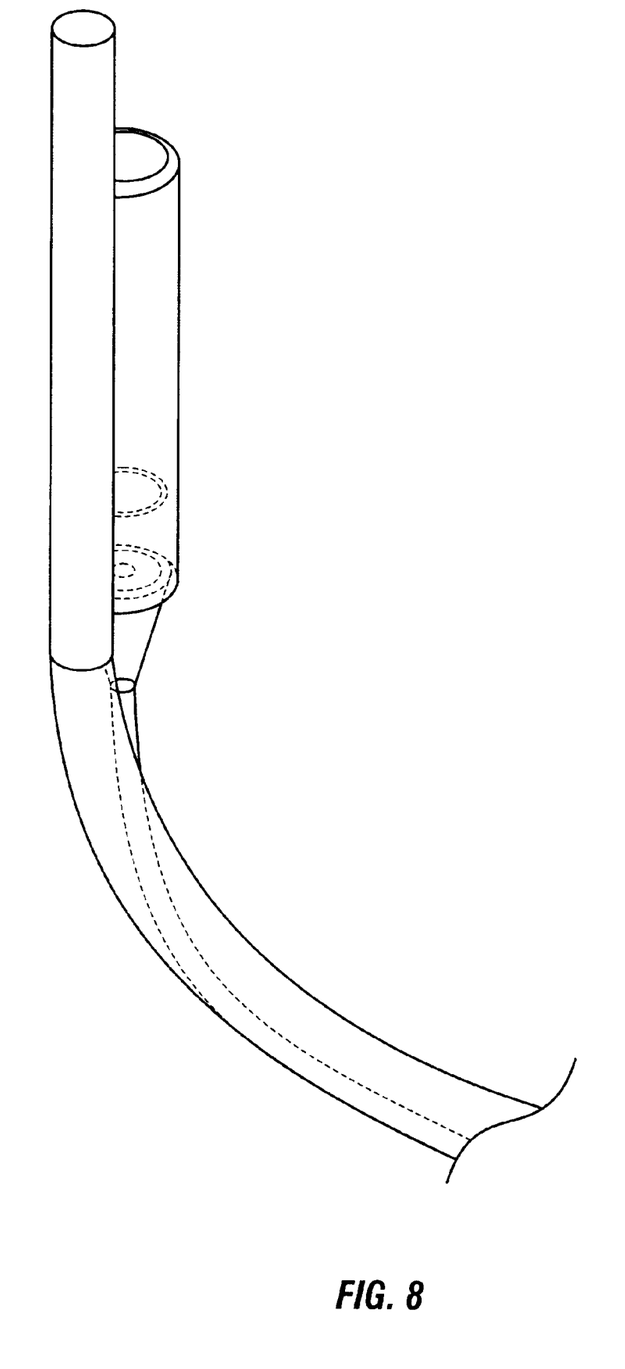
FIG. 8 is a perspective view of the embodiment of FIG. 7.

FIGS. 7 and 8 show an alternative embodiment of the present invention in which fiber optics 41 is provided to suction tip 12 (very close to or at the end of suction tip 12 (see FIG. 7)). Fiber optics 41 may be a single fiber optics fiber, or a bundle or cable of multiple fiber optics. Fiber optics 41 is activated at hand-held end 10 via a battery contained in housing 42. Fiber optics (and the light carried therewith) 41 go from housing 42 to suction tip 12 in fiber optics channel 44. Fiber optics channel 44 preferably follows the shape of and is preferably attached to casing 18 of laryngoscope. Size of fiber optics channel 44 is preferably minimized for the patient's airway. The material may be made of metal, stainless steel, plastic, ceramic or other materials, sufficient to house fiber optics 41. Fiber optics channel 44 may be rigid or flexible, depending on the material utilized. Casing 18, in all embodiments, is preferably rigid, but may be flexible.

During use of the laryngoscope, one emergency medical technician activates the light source so that he/she can see where to locate the laryngoscope in the airway of the patient. Once the laryngoscope is positioned, the operator can view or observe the source of debris or fluids, problem areas, and positioning. If an interchangeable tip is utilized, the operator can decide which tip to use, attach the selected tip to the laryngoscope, and then intubate the patient. If a flashlight is used as the light source, the operator can change out flashlights or flashlight bulbs when needed. The apparatus may be disposable or autoclaved for reuse.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, and of the corresponding application(s) are hereby incorporated by reference.

What is claimed is:

1. A lighted intubating laryngoscope comprising:
   an intubating laryngoscope comprising a hand-held end, a suction tip and an suction channel within a casing; and
   a light source outside said suction channel, said light source activated and operable by a single operator at said hand-held end for providing light to said suction tip while said laryngoscope is intubating a patient.

2. The laryngoscope of claim 1 wherein said light source comprises fiber optics.

3. The laryngoscope of claim 1 wherein said suction tip comprises a detachable suction tip.

4. The laryngoscope of claim 3 wherein said detachable suction tip is attached to said suction channel by an adhesive.

5. The laryngoscope of claim 1 wherein said light source is a flashlight.

6. The laryngoscope of claim 5 wherein said flashlight is activated by a push button.

7. The laryngoscope of claim 5 wherein said flashlight is attached to said hand-held end.

8. The laryngoscope of claim 7 wherein said flashlight is attached to said hand-held end by an adhesive.

9. The laryngoscope of claim 1 wherein said suction channel casing is made of a light-carrying material.

10. The laryngoscope of claim 9 wherein said suction channel casing is made of a transparent material.

11. The laryngoscope of claim 9 wherein said suction channel casing is made of an engineering plastic material.

12. The laryngoscope of claim 11 wherein said suction channel casing is made of a polycarbonate resin material.

13. The laryngoscope of claim 9 wherein said suction tip is made of a light-carrying material.

14. The laryngoscope of claim 13 wherein said light-carrying material comprises a transparent material.

15. The laryngoscope of claim 13, wherein said suction tip is configured to provide a selected illumination at said tip.

16. The laryngoscope of claim 15 wherein said light source provides diffused light at said suction tip.

17. A method of providing light to an intubating laryngoscope procedure comprising:
    providing an intubating laryngoscope comprising a hand-held end, a suction tip and an suction channel within a casing;
    providing a light source outside the suction channel, the light source activatable and operable by a single operator at the hand-held end for providing light to the suction tip; and
    intubating a patient while simultaneously providing the light source to the suction tip.

18. The method of claim 17 wherein the step of providing light comprises providing fiber optics.

19. The method of claim 17 wherein the step of providing a light source comprises providing a flashlight.

20. The method of claim 19 wherein the step of providing the flashlight comprises attaching the flashlight to the hand-held end.

21. The method of claim 17 further comprising the step of assembling a detachable tip as the suction tip onto the casing of the laryngoscope.

22. The method of claim 21 wherein the step of assembling the detachable tip onto the casing of the laryngoscope comprises selecting a detachable tip suitable for the age or size of the patient.

23. The method of claim 17 wherein the step of providing the laryngoscope comprises providing a laryngoscope with the suction channel casing made of a light-carrying material.

24. The method of claim 23 wherein the step of providing the casing with a light-carrying material comprises providing a transparent material.

25. The method of claim 23 wherein the step of providing the casing with a light-carrying material comprises providing an engineering plastic material.

26. The method of claim 25 wherein the step of providing the engineering plastic material comprises providing a polycarbonate resin material.

27. The method of claim 23 further comprising the step of providing the suction tip made of a transparent material.

28. The method of claim 27 wherein the step of providing the suction tip comprises providing a configuration for the suction tip to achieve a selected type of illumination.

29. The method of claim 28 wherein the step of configuring the suction tip comprises diffusing light from the light source at the suction tip.

* * * * *